(12) United States Patent
Friend et al.

(10) Patent No.: US 8,758,787 B2
(45) Date of Patent: Jun. 24, 2014

(54) LONG-LASTING INSECT REPELLANT, PESTICIDE AND ANTIFEEDANT COMPOSITIONS

(75) Inventors: Herman L. Friend, Rockville Center, NY (US); E. Cole Nelson, Jr., Village of Lakewood, IL (US)

(73) Assignee: Fasst Products, LLC., Rockville Centre, NY (US)

( * ) Notice: Subject to any disclaimer, the term of this patent is extended or adjusted under 35 U.S.C. 154(b) by 1224 days.

(21) Appl. No.: 11/949,482

(22) Filed: Dec. 3, 2007

(65) Prior Publication Data

US 2008/0132583 A1  Jun. 5, 2008

Related U.S. Application Data

(60) Provisional application No. 60/872,703, filed on Dec. 4, 2006.

(51) Int. Cl.
  *A01N 31/02* (2006.01)
  *A01N 25/18* (2006.01)

(52) U.S. Cl.
  USPC .......................................... 424/405; 514/739

(58) Field of Classification Search
  CPC ... A01N 2300/00; A01N 25/04; A01N 25/10; A01N 25/30; A01N 59/16; A01N 25/34; A01N 65/00; A01N 31/02; A01N 59/20; A01N 25/16; A01N 25/12; A01N 43/40; A01N 25/08; A01N 59/00; A01N 37/02
  USPC ....................................................... 424/405
  See application file for complete search history.

(56) References Cited

U.S. PATENT DOCUMENTS

| 4,732,762 | A |   | 3/1988 | Sjogren |
| 5,175,175 | A |   | 12/1992 | Wilson et al. |
| 5,679,129 | A |   | 10/1997 | Hon |
| 5,753,686 | A |   | 5/1998 | Marin et al. |
| 5,888,528 | A | * | 3/1999 | Wellinghoff et al. ......... 424/405 |
| 5,965,264 | A | * | 10/1999 | Barenberg et al. ............ 428/402 |
| 6,316,520 | B1 | * | 11/2001 | Hekal ............................ 523/102 |
| 6,932,099 | B2 | * | 8/2005 | Mahaney .................... 137/15.08 |
| 2006/0034898 | A1 | * | 2/2006 | Amodt et al. ................. 424/443 |

FOREIGN PATENT DOCUMENTS

JP   2002104904 A  *  4/2002

OTHER PUBLICATIONS

Sylosiv Molecular Sieve Powders, downloaded Nov. 28, 2007, available at www.gracedavison.com/eusilica/Adsorbents/product/sylosiv_molecular_sieve_powders.htm.
Zeolite Milecular Sieve, downloaded Nov. 28, 2007, available at www.gracedavison.com/eusilica/Adsorbents/product/zeolite_molecular_sieve.htm.
Material Safety Data Sheet, SA-15 PWD, UOP, Revision No. 1, Jun. 2007 (9 pages).

* cited by examiner

*Primary Examiner* — Janet Epps-Smith
*Assistant Examiner* — Audrea Buckley
(74) *Attorney, Agent, or Firm* — Gordon & Jacobson, PC

(57) ABSTRACT

An insect repellent material includes a carrier such as a polyethylene, a molecular sieve or zeolite material, and a repellent such as geraniol. The molecular sieve/zeolite material provides the insect repellent material with a slow-release quality and also permits the carrier to hold more insect repellent than it would otherwise if so desired.

9 Claims, 1 Drawing Sheet

Evaporation Test Results

LONG-LASTING INSECT REPELLANT, PESTICIDE AND ANTIFEEDANT COMPOSITIONS

CROSS-REFERENCE TO RELATED APPLICATIONS

This application claims benefits from U.S. Provisional Patent Application No. 60/872,703 filed Dec. 4, 2006, the contents of which are hereby incorporated herein by reference.

BACKGROUND OF THE INVENTION

1. Field of the Invention

This invention relates broadly to insect repellents, antifeedants and pesticides. More particularly, this invention relates to extended time release compositions and methods for repelling insects over an extended time. The invention has particular application to the repelling of the "red imported fire ant" *Solenopsis invicta* Buren, although it is not limited thereto.

2. State of the Art

The use of repellent composition materials such as GERANIOL COEUR (a trademark of International Flavors and Fragrances Inc.) to repel "red imported fire ants" (RIFA) is well known, and such compositions are commonly used for repelling insects and acting as antifeedants. See, e.g., U.S. Pat. No. 5,753,686. Geraniol is volatile, however, and must be replenished frequently, or the insect repellant loses its potency.

In an effort to extend the potency life of the insect repellency, geraniol has been combined with compatible carrier polymers such as high density polyethylene and low density polyethylene to form geraniol infused polyethylene pellets. See, e.g., U.S. Pat. No. 5,175,175 to Wilson et al. The advantages of this composition are improved handling and a greater length of time over which the pesticide/repellent is released under typical ambient conditions.

SUMMARY OF THE INVENTION

The present invention provides extended time release compositions and methods for repelling insects over an extended time.

The present invention also provides insect repellent compositions which have an extended life efficacy at elevated temperatures.

The present invention also provides long-lasting insect repellent compositions which are 25b EPA exempt.

According to one aspect of the invention, an insect repellent composition includes a polymer into which both a zeolite (molecular sieve material) and an insect repellent are incorporated. According to another aspect of the invention, the zeolite (molecular sieve material) and the insect repellent are matched so that the pore size of the zeolite (molecular sieve) is large enough to contain molecules of the insect repellent compound. For purposes of this application the terms "zeolite" and "molecular sieve" or "molecular sieve material" will be used interchangeably and are to be defined and understood to have the same meaning (i.e., a material containing tiny pores of generally precise and uniform size such that molecules small enough to pass through the pores are adsorbed while larger molecules are not), regardless of whether the zeolite or molecular sieve is a natural substance or a man-made substance.

In one embodiment, the insect repellent composition comprises a high density polyethylene, geraniol, and a molecular sieve which includes one or both of silicon oxide and aluminum oxide powder. According to another embodiment, an insect repellent is formed into pellets, pucks, or blocks having an approximate mixture of 30% insect repellent, 15% molecular sieve material, and 55% polymer by weight.

According to another aspect of the invention, an insect repellent composition having a polymer, a molecular sieve material, and an insect repellent is formed by co-extruding the ingredients. The co-extruded ingredients may be formed as pellets, ropes or strips, or molded into pucks or blocks of material, with the insect repellent being absorbed into the polymer matrix and the molecular sieve material. According to further aspect of the invention, the extrusion process is performed at a temperature above the melting point of the polymer and at a sufficient pressure to keep the insect repellent from evaporating.

According to yet another aspect of the invention, an insect repellent block formed from a polymer, an insect repellent, and a molecular sieve material and less than one cubic foot in volume is provided. The insect repellent block is placed in an electrical box which is subject to outdoor conditions and which regularly reaches temperatures exceeding 120° F., and generates insect repellent vapors for an extended period of approximately at least one year in sufficient quantities to repel target insects and prevent the insects from feeding on electrical wires, building nests or damaging the electronic equipment in the box.

Additional advantages of the invention will become apparent to those skilled in the art upon reference to the detailed description taken in conjunction with the provided figures.

DETAILED DESCRIPTION OF THE PREFERRED EMBODIMENTS

Figure 1:
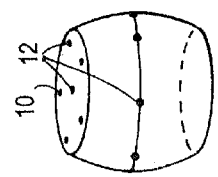
FIG. 1 is a perspective view of a block of the product of the invention.

In accord with a preferred embodiment of the invention, an improved extended time release, geraniol based, 25b EPA exempt repellent composition is provided which is also believed to act as an antifeedant and pesticide. The composition is effective in repelling the RIFA ("red imported fire ant") *Solenopsis invicta* Buren, and it is believed to be effective in repelling other insects as well. The preferred composition is comprised of polyethylene, a zeolite typically incorporating one or both of silicon oxide and aluminum oxide (e.g., an aluminosilicate), and geraniol. As set forth above, the word "zeolite" will be used interchangeably with "molecular sieve" and is to be understood to have the same meaning, regardless of whether the zeolite/molecular sieve is a natural substance or an man-made substance.

More particularly, in a presently preferred embodiment, high density polyethylene, a molecular sieve material having a unit cell size $A_0$ (i.e., vertex to vertex distance) of 24.29 Å, and a pore size of roughly 7.4 Å and sold as SA-15 PWD (a product of UOP—a Honeywell Company), and geraniol (available from International Flavors and Fragrances) are co-extruded and optionally molded as hereinafter described to generate a a mass of repellent material. For purposes herein the term "mass" of repellent material will be defined to include repellent material formed into any size or shape such as pellets (generally small and oval, round or bullet shaped), ropes, strips, pucks (generally molded into a cylindrical shape), and blocks (generally molded into a desired shape). The relative weights of the ingredients in the composition of the preferred embodiment are approximately: 25%-30% geraniol, 10%-15% molecular sieve material, and 65%-55% high density polyethylene.

In the presently preferred embodiment, the composition is formed by taking the high density polyethylene, the molecular sieve material, and the geraniol and extruding them in an extruder such as the Buss Co. Kneader Extruder. More particular, the high density polyethylene is heated above its melting point (e.g., between 220° F. and 250° F.), and added to the main hopper feeder. The geraniol is added through a downstream injection pin at a sufficiently high pressure to prevent the geraniol from evaporating during extrusion. The molecular sieve material is added through a downstream slide feeder. The operating temperature along the length of the extruder is typically between 280° F. and 300° F. The resulting co-extruded product is then cooled with the geraniol being contained in the polymer matrix and in the molecular sieve material (which is mixed with the polymer).

In one embodiment, the co-extruded product is pelletized using e.g., a Gala Underwater Pelletizer. Regardless of whether the product is pelletized or not, the coextruded product is optionally molded into blocks using a molder (e.g., an Arburg or Toshiba Molder) which can have multiple heating zones. Once formed into its desired shape, the mass of repellent material is preferably wrapped in cellophane, a vapor bag, or is placed in a container to prevent escape of the geraniol from the mass.

According to another embodiment, rather than co-extruding the high density polyethylene, the molecular sieve material, and the geraniol as described above, the molecular sieve material and the geraniol are first mixed such that the geraniol is at least partially adsorbed in the molecular sieve material. The resulting mixture or slurry may then be co-extruding or mixed in a batch process with the melted polyethylene in a sufficiently high pressure environment to prevent the geraniol from evaporating during the procedure. The resulting material is then formed into a desired shape (e.g., pellets, rope, strip, puck, or block) and size and cooled. The resulting repellent mass is then preferably wrapped in cellophane a vapor bag, or is placed in a container to prevent escape of the geraniol from the mass.

It will be appreciated that where the geraniol is completely adsorbed by the molecular sieve material during co-extrusion with the melted polyethylene (or during pre-mixing), the melted polyethylene will act as a carrier for the molecular sieve material which holds the geraniol and will not separately carry the geraniol (although, of course, as geraniol leaves the molecular sieve material it will migrate through the polyethylene). However, where the amount of geraniol exceeds the capacity of the molecular sieve material to adsorb all of the geraniol, the melted polyethylene will not only carry the molecular sieve material which has adsorbed geraniol, but will also separately carry the geraniol. As a result, as will be described hereinafter, when the geraniol is totally adsorbed in the molecular sieve, the rate of release of geraniol will remain relatively constant, whereas, when the geraniol is both adsorbed by the molecular sieve and separately contained in the polyethylene, geraniol will be released initially at a much higher rate, and then the rate of release will slow and remain relatively constant.

In one preferred embodiment, where the composition is to be used as an insect repellent in an electrical box which is subject to outdoor conditions and which regularly reaches temperatures exceeding 120° F., and where insect repellent vapors are needed for an extended period of approximately at least one year in sufficient quantities to repel target insects and prevent the insects from feeding on electrical wires in the box, a block or puck 10 of less than one cubic foot of material is formed as seen in FIG. 1. More particularly, the puck 10 of FIG. 1 is a molded block having a beer barrel shape with top and bottom diameters of approximately 1.25 inches, a center diameter of 1.5 inches, a height of 1.25 inches (for a total volume of between 2 and 3 cubic inches), and weighing approximately 36 grams. The puck 10 has a series of 1/16 inch protruding nubs 12 at the top and bottom surfaces and around the periphery of the center line which minimize surface contact and enable unhindered flow of active ingredient out of the block.

It should be appreciated that the molecular sieve material significantly increases the amount of liquid geraniol which can be added to the polymer and retained therein. In particular, without the molecular sieve material, the amount of liquid geraniol that is readily added to high density polyethylene is approximately 20% by weight of the geraniol-polyethylene mixture. By adding 10% by weight of the SA-15 PWD molecular sieve material, the molecular sieve itself can optimally adsorb about 10% by weight of the geraniol, and therefore the amount of liquid geraniol that can be added to the compound increases to approximately 26% by weight of the geraniol-molecular sieve-polyethylene mixture (as the polyethylene will itself be able to hold a little less due to its decreased amount in the compound). By adding 15% by weight of molecular sieve material, the amount of liquid geraniol that can be added increases to approximately 29% by weight of the geraniol-molecular sieve-polyethylene mixture. In some cases, it may be possible to provide a molecular sieve material which constitutes 25% by weight of the composition, and in such cases, the amount of geraniol that can be added could increase to approximately 35%. Thus, by adding the molecular sieve material to the polyethylene, the polyethylene and molecular sieve material can be loaded with significantly more geraniol. In addition, because the molecular sieve material is believed to reduce the essential oil vapor pressure of the geraniol as the energy state of the geraniol is reduced as it enters the cage structure of the molecular sieve, the rate of evaporation of the geraniol from the repellent material is reduced, thereby extending the product life and repellent efficacy of the composition.

Figure 2:
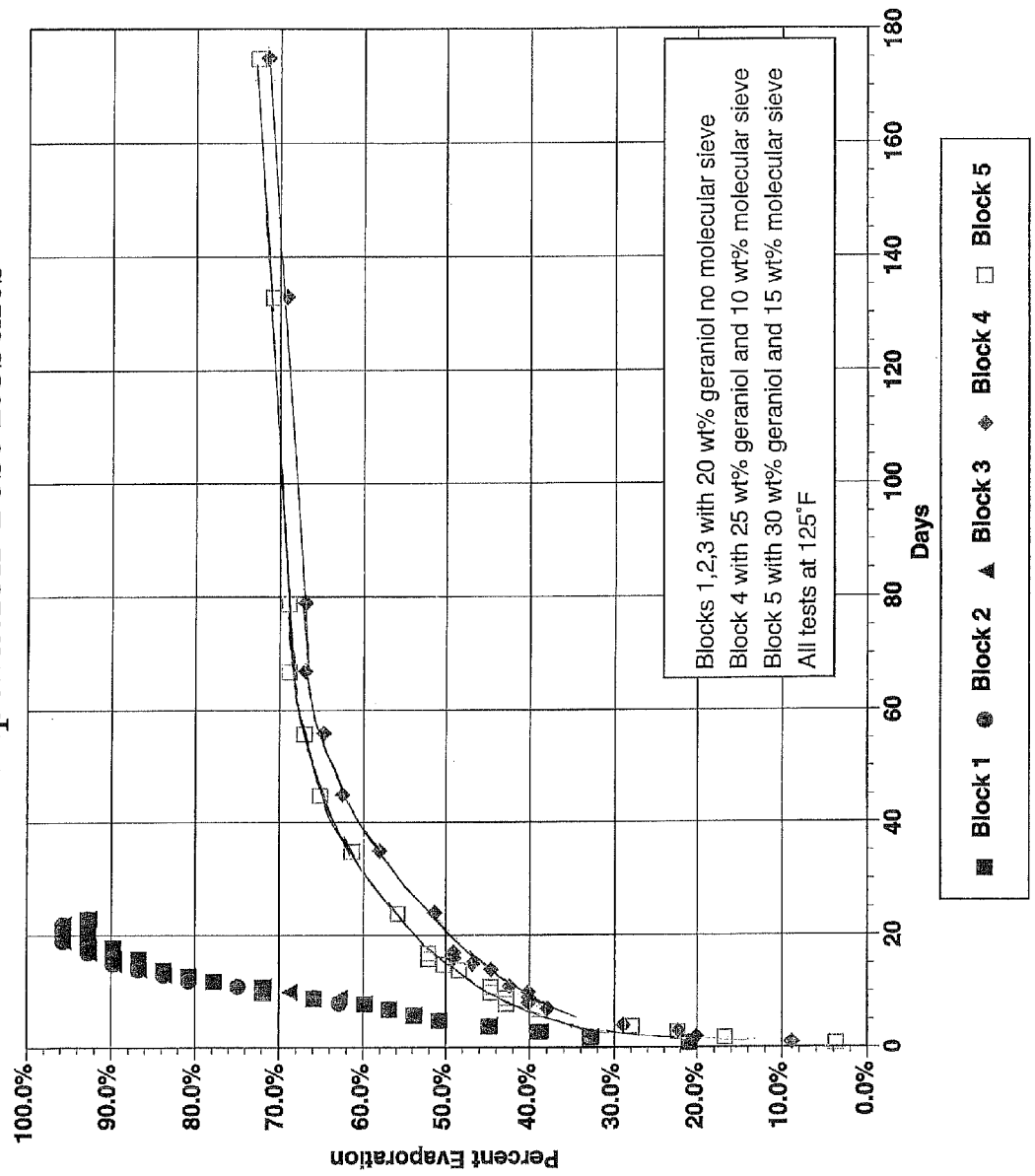
FIG. 2 is a graph of evaporation test results comparing the prior art with the composition of the invention.

FIG. 2 is a graph which shows the reduced rate of evaporation of geraniol from a composition comprised of the geraniol, high density polyethylene, and the SA-15 PWD molecular sieve material, relative to the evaporation of geraniol from a repellent material containing geraniol and polyethylene and no molecular sieve material. More particularly, five blocks of repellent material were made, each half in thick, two inches long and one inch wide. Blocks 1, 2, and 3 were made out of high density polyethylene loaded with 20% by weight geraniol and weighed 16.7 grams. Block 4 was made out of high density polyethyelene with 10% by weight SA-15 PWD molecular sieve material and 25% by weight geraniol. Block 5 was made out of high density polyethyelene with 15% by weight SA-15 PWD molecular sieve material and 30% by weight geraniol. All five blocks were placed in a 125° F. oven and tested regularly to see the percent evaporation of the geraniol over time (by removing the blocks and weighing them). As seen in FIG. 1, before day 20, 90% of the geraniol in blocks 1, 2, and 3 had already evaporated, and by day 25, 95% of the geraniol in all three blocks had evaporated. Thus, by day 25, the repellent material of blocks 1, 2, and 3 contained only approximately 5% of its original geraniol, which constituted about 1% of the block by weight. In contrast, by day 20, block 4 retained about 50% of its geraniol and block 5 retained about 45% of its geraniol. Thus, at day 20, the geraniol in block 4 constituted about 12.5% (50% of 25%) of the block by weight, and the geraniol in block 5 constituted about 13.5% (45% of 30%) of that block by weight. At day 60, block 4 retained about 34% of its geraniol, and block 5 retained about 32% of its geraniol. Thus at day 60, the geraniol in block 4 constituted about 8.5% of the block by weight, and the geraniol in block 5 constituted about 9.6% of the block by weight.

Starting at about day 60 (and certainly at day 90 or day 120), it is seen that each of blocks 4 and 5 lost about 0.04% of their original geraniol per day (about 4% over 100 days). Thus, it is believed that had tests continued for another 190 days past the 175 days shown, each block (at 365 days or 1 year) would have retained about 25% of its original geraniol (which in the case of block 4 would be about 7% of the block by weight, and in the case of block 5 would be about 7.5% of the block by weight). Similarly, at 2 years, each block would have retained about 10% of its original geraniol, which in the case of block 4 would be about 2.5% of the block by weight, and in the case of block 5 would be about 3% of the block by weight. In addition, it is believed that the 0.04% daily geraniol loss is associated almost exclusively with geraniol escaping from the molecular sieve material, as the geraniol contained in the high density polyethylene and not trapped by the molecular sieve would have almost entirely evaporated by day 20 as shown by the data for blocks 1, 2, and 3. Therefore, provided a sufficient mass of material is utilized, the continuing 0.04% daily (of original content) geraniol loss will be sufficient to repel insects in limited areas.

Based on the above, according to a method of the present invention, a repellent block of material containing preferably 25%-30% geraniol, 10%-15% molecular sieve material, and 65%-55% high density polyethylene, and preferably formed by co-extruding in a high pressure environment, is taken (unwrapped when appropriate) and placed in an electrical box which is subject to outdoor conditions and which regularly reaches temperatures exceeding 120° F. The repellent block of material is left in the box for at least 180 days, and preferably up to one year, and possibly up to two years or more, and then replaced with another repellent block of material. When the repellent block is placed in the box, the geraniol in the repellent block initially quickly, and then slowly evaporates and provides insect repellent vapors in sufficient quantities to repel target insects and prevent the insects from feeding on electrical wires, building nests, and damaging electronic equipment in the box. Preferably, the block of material comprises less than one cubic foot of material. In certain standard electrical boxes, it has believed that a block (mass) of between 2 and 3 cubic inches of material is sufficient to drive the RIFA out of the box and keep the box clean from RIFA damage over a period of one year.

While the presently preferred embodiment of the invention in comprises high density polyethylene, a molecular sieve material sold as SA-15 PWD, and geraniol, other embodiments of the invention provide different carrier materials, different molecular sieve materials, and different repellent, antifeedant or pesticide materials. More particularly, other polymers such as low density polyethylene, polystyrene, polypropylene, ABS, silicone, polyurethane, and polyvinylchloride could be used instead of high density polyethylene. Also, while less preferred, instead of a polymer, other carriers such as cotton or a clay binder could be utilized. Similarly, different and/or additional molecular sieves may be used instead of the SA-15 PWD. Likewise, other insect repellents, antifeedants, and pesticides may be used instead of or in addition to the geraniol. These additional insect repellents, antifeedants and pesticides include (by way of example only) D-limonene, permethrin or permethrin variations, oil of citronella, pyrethrum (from chrysanthemum flowers) or pyrethroids, neem oil, DEET, registered pesticides, and Federal Insecticide Fungicide, Rodenticide Act (FIFRA) EPA 25b registration exempt materials.

Where an insect repellent, antifeedant or pesticide other than or in addition to geraniol is used, according to one aspect of the invention, the molecular sieve is preferably chosen to match that insect repellent, antifeedant or pesticide. More particularly, molecular sieves have specific pore sizes, and different insect repellents, antifeedants and pesticides have different molecule compound sizes. It is believed that it is important to match the pore size of the molecular sieve to the molecule size of the insect repellent, antifeedant or pesticide so that at least the active portion of the insect repellent, antifeedant, or pesticide can be adsorbed by the molecular sieve. Thus, if a combination is used of insect repellents, antifeedants and/or pesticides having different molecular sizes, more than one molecular sieve material should be used to match respective molecular sizes if the slow release aspect of each of the utilized ingredients is to be maintained. If desired, however, it is possible to provide one or more insect repellents, antifeedants, and/or pesticides in the carrier, while maintaining a different insect repellent, antifeedant, and/or pesticide in the molecular sieve.

It will also be appreciated by those skilled in the art, that while a particular co-extrusion process and a particular batch process were described, there are other manners of combining the molecular sieve and carrier. For example, a sieve powder can be mixed with a binder such as clay or alumina. The resultant mixture can then formed into a desired shape and heat-treated to obtain structural integrity. The repellent can then added to the cooled product and adsorbed by the molecular sieve.

There have been described and illustrated herein several embodiments of an insect repellent material and a method of making and using the same. While particular embodiments of the invention have been described, it is not intended that the invention be limited thereto, as it is intended that the invention be as broad in scope as the art will allow and that the specification be read likewise. Thus, while particular carriers, molecular sieves, and insect repellents, antifeedants and pesticides have been disclosed, it will be appreciated that others could be used as well. Also, while certain preferred weight percentages for the molecular sieve and the insect repellent were described, it will be appreciated that other percentages could be used. With respect to the insect repellent, those percentages preferably, but not necessarily, exceed the maximum percentages that can be infused in the carrier without the molecular sieve. Further, while the insect repellent material was described as being formed in pellets, ropes, strips, pucks, or blocks or certain sizes, it will be appreciated that other shapes may be formed and different size units may be manufactured, and that the term "mass" as used herein is intended to encompass the material formed into any shape and size. Additionally, while the insect repellent material was described as directed to repelling the RIFA *Solenopsis invicta* Buren, it will be understood that the insect repellent material could be used to repel or kill other insects. Furthermore, while the insect repellent material was described as being placed in electrical boxes which are subject to outdoor conditions and which regularly reach temperatures exceeding 120° F., it will be appreciated that the insect repellent material can be placed in other locations and in boxes where the temperature reaches only 100° F., or only 80° F. or does not reach so high, or reaches temperatures higher than 120° F. Further yet, while a composition useful for one year or more as an insect repellent was described as having a 0.04% daily (of original content) loss of its repellent ingredient after 60 days, it will be appreciated that depending upon the size of the block and its application, different repellents and different molecular sieves may be chosen so that the daily loss of original repellent content from the molecular sieve might be different (typically in the range of 0.02% and 0.1%—by way of example and not by way of limitation) and still have the desired efficacy. Likewise, while the polyethylene was described as retaining the repellent for twenty days, other polymers could be chosen which might retain repellency for shorter or longer periods of time. It will therefore be appreciated by those skilled in the art that yet other modifications could be made to the provided invention without deviating from its spirit and scope as claimed.

What is claimed is:

1. A method, comprising:
    obtaining a mass of a composition exhibiting insect repellent, antifeedant or pesticide activity and comprising a carrier, an insect repellent, antifeedant or pesticide, and a molecular sieve material which has adsorbed at least some of said insect repellent, antifeedant or pesticide, wherein said molecular sieve material and said insect repellent, antifeedant or pesticide are chosen such that after 90 days of use, said insect repellent, antifeedant or pesticide evaporates by diffusion and not by chemical reaction from said molecular sieve material at a daily loss of original insect repellent, antifeedant or pesticide content in the range of 0.02% and 0.1% for at least 90 days;
    placing said mass in an electrical box containing electrical wires and which is subject to outdoor conditions and which regularly reaches temperatures exceeding 120° F. in order to keep insects away from said electrical wires; and
    leaving said mass in said electrical box for at least 180 days, wherein said insect repellent, antifeedant or pesticide evaporates by diffusion and not by chemical reaction at said daily loss for at least 90 days.

2. A method according to claim 1, wherein:
    said at least 180 days comprises at least one year, and said method further comprises replacing said mass with another repellent mass comprised from said composition.

3. A method according to claim 1, wherein:
    said mass has a volume of less than one cubic foot.

4. A method according to claim 1, wherein:
    said carrier is chosen from high density polyethylene, low density polyethylene, polystyrene, polypropylene, ABS, silicone, polyurethane, and polyvinylchloride, and
    said insect repellent, antifeedant, or pesticide is chosen from geraniol, D-limonene, permethrin, oil of citronella, pyrethrum, and neem oil.

5. A method according to claim 1, wherein:
    said composition includes at least two insect repellents, antifeedants, and/or pesticides, wherein at least one of said at least two is adsorbed by said molecular sieve material such that after 90 days of use, said at least one insect repellent, antifeedant or pesticide evaporates by diffusion and not by chemical reaction from said molecular sieve material at said daily loss.

6. A method of repelling fire ants, comprising:
    obtaining a block of a composition having a polyethylene carrier being at least 40% by weight of the composition as originally manufactured, a molecular sieve material being at least 10% by weight of the composition as originally manufactured, and geraniol being at least 25% by weight of the composition as originally manufactured; and
    placing said block of composition in an electrical box containing electrical wires and which is subject to outdoor conditions and which regularly reaches temperatures exceeding 120° F. for at least 180 days prior to removal whereby a sufficient amount of said geraniol evaporates out of said block by diffusion and not by chemical reaction in order to repel the fire ants.

7. A method according to claim 6, wherein:
    said molecular sieve material has a pore size of approximately 7.4 Å.

8. A method according to claim 6, wherein:
    said block was manufactured by extruding said polyethylene carrier, said molecular sieve material and said geraniol under a sufficiently high pressure to prevent said geraniol from evaporating.

9. A method according to claim 1, wherein:
    said molecular sieve material has a pore size of approximately 7.4 Å.

* * * * *